US008513711B2

(12) United States Patent
Kunz et al.

(10) Patent No.: US 8,513,711 B2
(45) Date of Patent: Aug. 20, 2013

(54) GAS-SENSITIVE SEMICONDUCTOR DEVICE

(75) Inventors: Denis Kunz, Malsch (DE); Markus Widenmeyer, Schoenaich (DE); Alexander Martin, Regensburg (DE)

(73) Assignee: Robert Bosch GmbH, Stuttgart (DE)

( * ) Notice: Subject to any disclaimer, the term of this patent is extended or adjusted under 35 U.S.C. 154(b) by 226 days.

(21) Appl. No.: 12/924,284

(22) Filed: Sep. 23, 2010

(65) Prior Publication Data

US 2011/0121368 A1 May 26, 2011

(30) Foreign Application Priority Data

Oct. 8, 2009 (DE) .................. 10 2009 045 475

(51) Int. Cl.
*H01L 21/00* (2006.01)
(52) U.S. Cl.
USPC ............................ 257/253; 257/252; 257/414
(58) Field of Classification Search
USPC ......................................... 257/252–253, 414
See application file for complete search history.

(56) References Cited

U.S. PATENT DOCUMENTS

| 4,020,830 A | * | 5/1977 | Johnson et al. ............... 600/348 |
| 4,158,807 A | | 6/1979 | Senturia |
| 4,180,771 A | * | 12/1979 | Guckel .......................... 324/71.1 |
| 4,198,851 A | * | 4/1980 | Janata ............................ 73/31.06 |
| 4,218,298 A | * | 8/1980 | Shimada et al. ............... 257/253 |
| 4,264,728 A | * | 4/1981 | Wilkins ............................ 435/5 |
| 4,269,682 A | * | 5/1981 | Yano et al. ..................... 204/418 |
| 4,273,636 A | * | 6/1981 | Shimada et al. ............... 204/415 |
| 4,322,680 A | * | 3/1982 | Janata et al. ................... 324/71.2 |
| 4,354,308 A | * | 10/1982 | Shimada et al. ............... 438/49 |
| 4,385,274 A | * | 5/1983 | Shimada et al. ............... 324/71.6 |
| 4,397,714 A | * | 8/1983 | Janata et al. ................... 205/775 |
| 4,411,741 A | * | 10/1983 | Janata ............................ 257/253 |
| 4,671,852 A | * | 6/1987 | Pyke ............................... 438/49 |
| 4,764,797 A | * | 8/1988 | Shaw et al. .................... 257/253 |
| 4,947,104 A | * | 8/1990 | Pyke ............................... 324/71.5 |
| 5,063,081 A | * | 11/1991 | Cozzette et al. ................. 435/4 |
| 5,212,050 A | * | 5/1993 | Mier et al. ..................... 430/320 |
| 5,786,235 A | * | 7/1998 | Eisele et al. .................... 438/53 |
| 5,911,873 A | * | 6/1999 | McCarron et al. ............ 205/789 |
| 6,306,594 B1 | * | 10/2001 | Cozzette et al. ............ 435/6.11 |
| 6,521,109 B1 | * | 2/2003 | Bartic et al. ............. 204/403.01 |
| 6,955,749 B2 | * | 10/2005 | Frerichs ....................... 204/416 |
| 7,151,301 B2 | * | 12/2006 | Yoo et al. ..................... 257/401 |
| 7,662,341 B2 | * | 2/2010 | Eversmann et al. ........ 422/82.02 |
| 8,263,336 B2 | * | 9/2012 | Rothberg et al. ............. 435/6.1 |
| 2005/0235735 A1 | * | 10/2005 | Doll et al. ..................... 73/31.06 |
| 2010/0300895 A1 | * | 12/2010 | Nobile et al. ................. 205/775 |

(Continued)

FOREIGN PATENT DOCUMENTS

DE 196 13 274 10/1997
DE 10 2004 013 678 10/2005
WO WO 2007/009948 1/2007

*Primary Examiner* — Laura Menz
(74) *Attorney, Agent, or Firm* — Kenyon & Kenyon LLP

(57) ABSTRACT

A gas-sensitive semiconductor device having a semiconductive channel (10) which is delimited by a first (12) and a second (14) channel electrode, and having a gate electrode (16) which is associated with the channel and which cooperates with the channel in such a way that a change in conductivity of the channel (10) occurs as a response to an action of a gas. The gate electrode (16) and/or a gate insulation layer (20) which insulates the gate electrode from the channel, and/or a gate stack layer (18) which may be provided between the gate electrode and the channel have/has two surface sections (22, 24) which differ in their sensitivity to gases.

18 Claims, 4 Drawing Sheets

(56) References Cited

U.S. PATENT DOCUMENTS

| | | | |
|---|---|---|---|
| 2011/0121368 A1* | 5/2011 | Kunz et al. | 257/253 |
| 2011/0198674 A1* | 8/2011 | Krauss et al. | 257/253 |
| 2011/0260219 A1* | 10/2011 | Wahl et al. | 257/253 |
| 2012/0045368 A1* | 2/2012 | Hinz et al. | 422/69 |

* cited by examiner

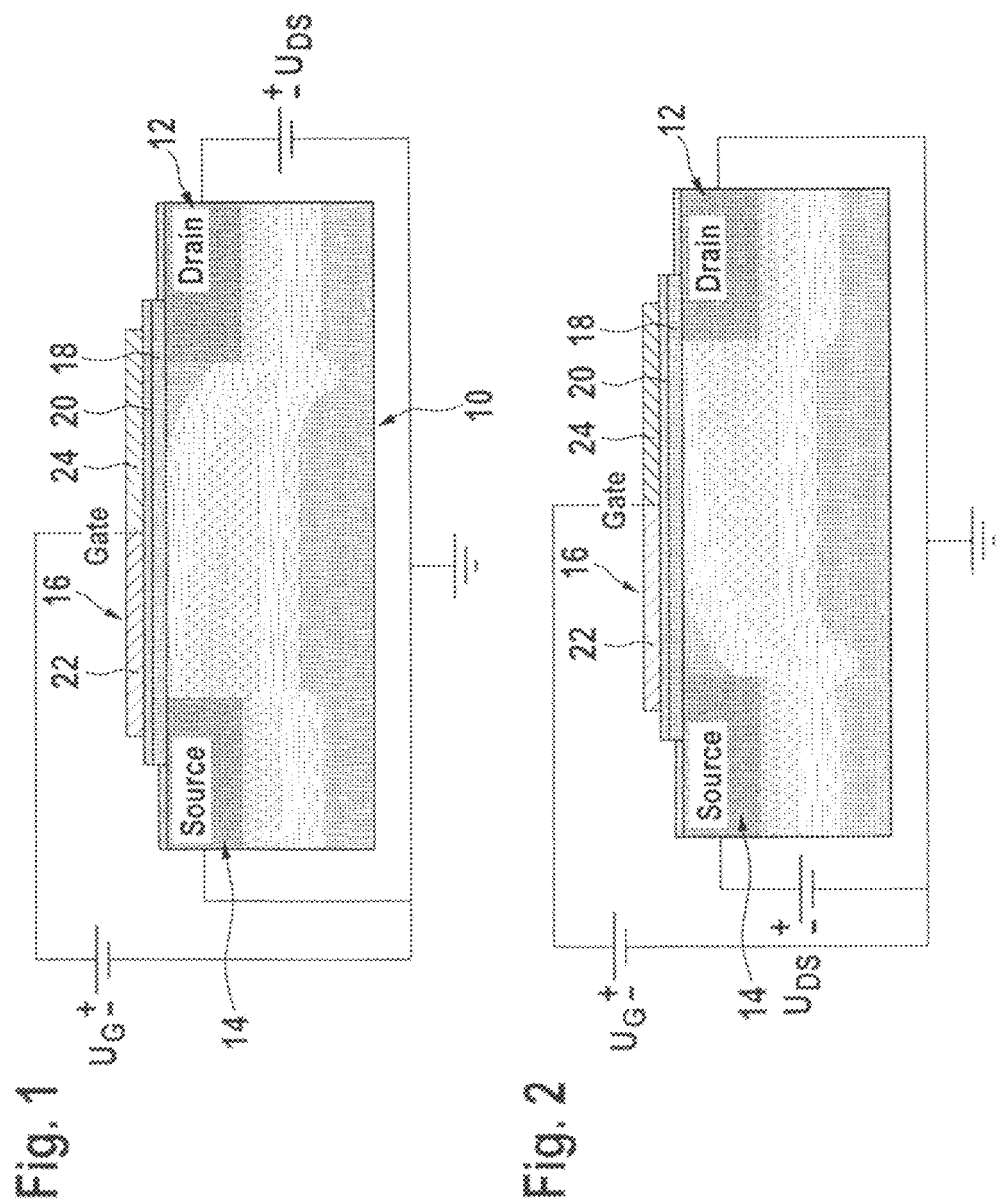

GAS-SENSITIVE SEMICONDUCTOR DEVICE

BACKGROUND OF THE INVENTION

1. Field of the Invention

The present invention relates to a gas-sensitive semiconductor device. Moreover, the present invention relates to the use of such a device.

2. Description of Related Art

This type of device is generally known from the related art, and is described, for example, as a so-called CHEMFET in U.S. Pat. No. 4,411,741.

This technology, which is used to define the species and is presumed as the current related art, relates to gas-sensitive semiconductor components having a gas-sensitive layer whose electrical properties may be altered by absorption or adsorption of gas, and which have an effect on the electronic behavior of the semiconductor component, in particular a change in conductivity of the semiconductive channel, with the effect that, for example, as a response to an acting gas to be detected, the current flowing between the first channel electrode (drain, for example) and the second channel electrode (source) is altered.

In particular, in the related art use is made of the effect that an interaction of gas molecules, to be detected, with a gate electrode which is catalytically active, for example, causes a change in the effective applied gate potential which in the manner described brings about a signal change of a drain-source current as a typical (sensor) measuring signal or detection signal.

It is known from the related art to induce selectivity with respect to certain gases, i.e., to allow the described interactions which cause the change in conductivity only for certain gases or gas mixtures, by selecting or installing suitable gate electrode materials.

However, it is difficult to clearly and distinctly develop such selectivities with respect to a single gas species, which usually results in undesired influences (cross-sensitivities) due to additional gas components. In this regard, it is known from the related art to compensate for such superimposed (and undesired) signals generated in this manner, using electronic or computational means, it being common in particular to detect the various gas species with the aid of a detector field of a plurality of CHEMFETs (as a sensor array) having different sensitivities, in order to then ascertain the desired information from the individual sensor signals in downstream evaluation units, using computational means. Aside from the associated complexity of evaluation, complicated multiplexer technology and/or multiple electrical feed lines to each individual CHEMFET are/is necessary for the signal transmission.

SUMMARY OF THE INVENTION

The object of the present invention, therefore, is to improve a gas-sensitive semiconductor device, in particular a gas-sensitive semiconductor component as a CHEMFET, with regard to signal generation and signal evaluation which is simple and reliable, and for which compensation is not very complicated.

The object is achieved using the gas-sensitive semiconductor component of the present invention. In an advantageous manner according to the present invention the gate electrode (additionally or alternatively the gate insulation layer, additionally or alternatively the optionally providable gate stack layer) is provided with two surface sections in such a way that these two surface sections form a (shared) gate electrode having sensitivity to various gases. Thus, in effect the functionality of two known semiconductor components is implemented in a shared integrated device, which together with the two surface sections has the particular discretely known, predetermined, or established sensitivity characteristics. Within the scope of the present invention and with regard to the surface sections according to the present invention, "sensitivity" is understood to mean the ability of these surface sections to absorb a gas or multiple suitable gases, and as a response to the absorption to cause a change in characteristics which has an effect on the change in conductivity of the semiconductive channel in the manner described according to the present invention.

A semiconductor device implemented in this way according to the present invention, in particular implemented as an individual semiconductor component, for example, a CHEMFET, thus allows one of the two surface sections to be selectively activated and allowed to interact with a gas to be detected as the result of suitably connecting the first and second channel electrodes, in particular connecting to a voltage in two different polarities corresponding to a particular operating mode. A semiconductor device as claimed according to the present invention is thus provided which, corresponding to the two surface sections, may have its gas sensitivity switched, which is to be activated by the sensitivity of a particular surface section as the result of wiring (more precisely, the polarity of an applied channel voltage).

This principle according to the present invention is based on the finding, claimed separately from the present invention, that, depending on the polarity of the channel voltage (and the depletion zone which is thus created in the region of the first and second channel electrodes in the semiconductive channel), the gas-sensitive effect of a gate electrode having a suitably gas-sensitive design acts only in the depletion region. In other words, when a gas-sensitive semiconductor device according to the present invention, in particular implemented as a CHEMFET at the working point, only the depleted channel region contributes to the sensor signal (i.e., to the change in conductivity) when it is acted on by a gas to be detected.

This finding is utilized according to the present invention in that the two surface sections are advantageously located in such a way that, corresponding to a particular wiring state (and to a depletion zone thus produced in the channel), only one of the two particular locally associated surface sections is active, and using appropriate gas detection is able to influence the conductive characteristics of the semiconductor.

Further advantages, features, and particulars of the present invention result from the following description of preferred exemplary embodiments and with reference to the drawings.

BRIEF DESCRIPTION OF THE DRAWINGS

FIG. 1 shows a schematic illustration of a gas-sensitive semiconductor device as a CHEMFET, according to a first preferred specific embodiment in a first operating mode.

FIG. 2 shows an illustration of the first exemplary embodiment similar to FIG. 1, but in the second operating mode.

DETAILED DESCRIPTION OF THE INVENTION

Figure 3:
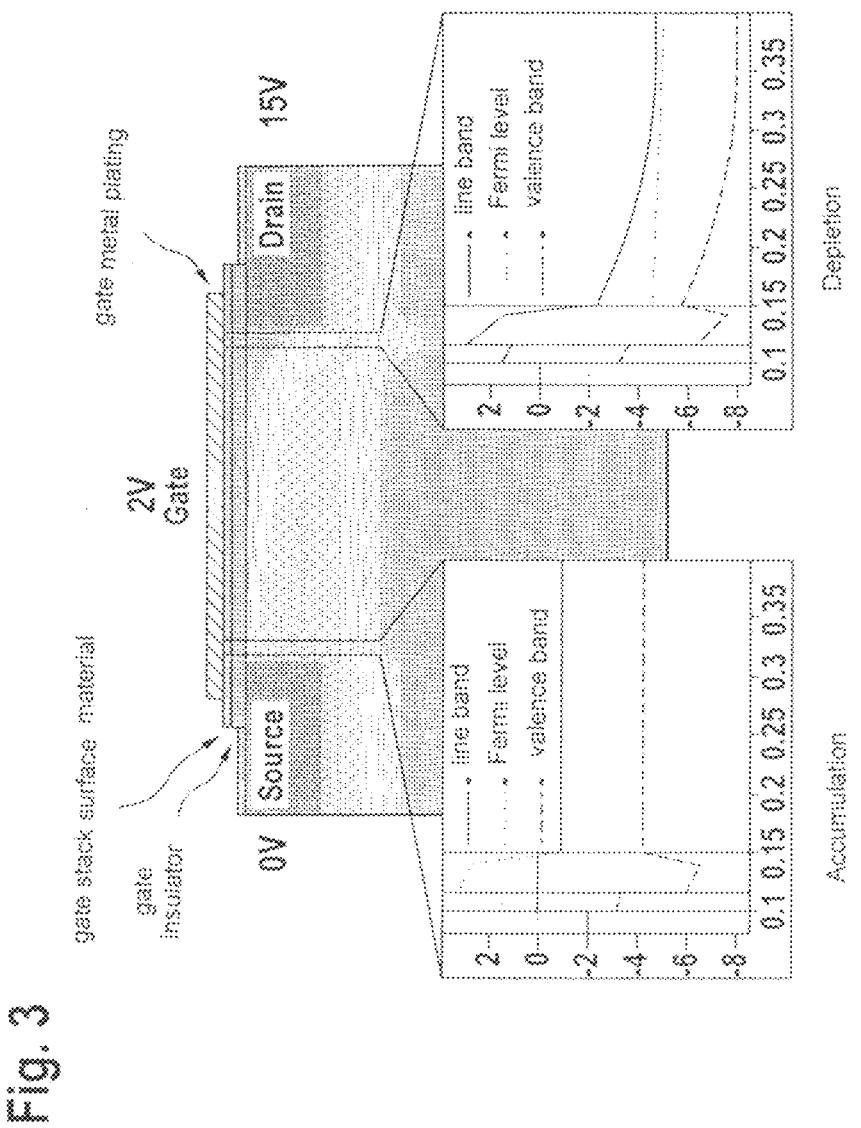
FIG. 3 shows a schematic illustration for clarifying the concentration of electrons in the semiconductor channel.

According to the present invention, it is first provided and preferred to divide the two surface sections according to the present invention approximately in the middle, along the direction of the extension of the channel, resulting in a symmetrical configuration. Nevertheless, it is within the scope of the present invention, and advantageous in refinements depending on the individual case (in particular, also on the characteristics of a particular depletion zone), to provide the region junction between the two surface sections closer to one of the two channel electrodes.

For the advantageous implementation of the present invention within the scope of a CHEMFET architecture, it is preferred first of all that the gate electrode (additionally or alternatively, in particular for a porous and thus gas-permeable gate electrode) also has a surface of the gate insulation layer or a gate stack layer, two different metals or metal alloys corresponding to a particular different adsorption characteristic for the desired gas selectivity. Such metals, metal alloys, or dopings are generally known from the related art.

Additionally or alternatively, in one advantageous refinement of the present invention it is advantageous to provide (only) one of the two surface sections of the gate electrode with a gas-tight ("gas-blind") design, for this purpose the gate surface being metal-plated using a closed metal film, optionally an additional passivation layer, while the second half of the gate region is provided with a gas-sensitive (typically a porous, catalytically active) metal layer.

To implement the capability according to the present invention for switching the sensitivities to various gases corresponding to the two surface sections, for the sensor operation and in the refinement according to the present invention it is provided to wire the semiconductor device using means for adjusting the working point, which are able to select and control the detection effect between the two surface sections by the application or controlled reversal of the polarity between the two channel electrodes. Thus, in a first operating mode according to the present invention, using a first electrical voltage (typically a source-drain voltage) of the first polarity, a first of the surface sections is activated, namely, the section of the gate electrode situated above a depletion region which is produced in this way in the channel. A detection electronics system advantageously provided downstream may then suitably detect a sensor signal, for example, the current flowing between the drain and the source. For activating the second surface section while simultaneously deactivating the first surface section, in the second operating mode the voltage applied to the channel electrodes would be reversed from the first polarity to the second polarity, so that the depletion zone migrates to the opposite end of the channel and accordingly activates the surface section which is located at that site. A sensitivity according to the present invention which is different with respect to the first surface section then results in a modified sensor signal which may be appropriately evaluated.

In the further evaluation, not only is it possible and advantageous to thus generate measuring signals for two different gases (i.e., the particular associated concentrations, for example) using only one semiconductor element, but, to solve the problem described at the outset with regard to the related art, a simple and reliable compensation is also possible: namely, when, for example, a first of the two surface sections is sensitive to NO as a gas, while the second of the two surface sections is sensitive to a gas mixture, in this case NO and $NO_2$, using an appropriate unit, the present invention allows a $NO_2$ detection signal to be easily ascertained (and thus allows an elegant compensation of the cross-sensitivity described at the outset) by subtracting the signals generated in the two operating modes (thus reducing the influence of NO to zero). Such a procedure is particularly beneficial and advantageous, for example, with regard to the fact that for a traditional implementation of such a measurement with the aid of two discrete components, it would be necessary to take into account the particular component tolerances and possibly different aging characteristics of the sensors, which are dispensed with in the implementation according to the present invention, using only one component.

Thus, by use of the present invention, first of all it is possible in an obvious manner in the implementation of (traditionally necessary) multi-element sensor fields to achieve a significant reduction in hardware complexity, not only for the semiconductor components themselves, but also for associated connections, cables, multiplexer technologies, or the like. In fact, there is also a savings of semiconductor surface area which in turn reduces costs, and with regard to the spatially limited installation conditions results in completely novel possibilities.

Thus, the present invention is suited in principle for practically any given, preferably complex, gas sensor system applications which are suited to the generic principle. Not least of all, however, as a result of the compact and efficient physical implementation, use in the automotive field, in particular in conjunction with exhaust gas measurement, i.e., measurement of hot gases in corrosive environments, has proven to be particularly advantageous and preferable.

FIG. 1 schematically shows the design and wiring of a gas-sensitive semiconductor device according to a first exemplary embodiment of the present invention: a CHEMFET composed of a semiconductive channel 10, a drain electrode 12 (first channel electrode), a source electrode 14 (second channel electrode), and a gate electrode 16 divided into two sections with a gate insulator layer 20 and gate stack surface layer 18 therebetween is provided on the gate, with different gate metal platings on each side. In the present exemplary embodiment, metallic gate 16 is divided into two surface sections 22, 24, resulting in a region junction in the center, between the drain and the source and transverse to the direction of the channel extension (and therefore perpendicular to the plane of the figure). A first of the two surface sections 22, 24 is plated using metals, metal cermets, or alloys of Pt, Pd, Au, Ag, Ir, Ti, Mn, Ni, Rh, Ru, Re, for example, for producing a first sensitivity, for example with respect to NO, while the second of surface sections 22, 24 is plated using metals, metal cermets, or alloys, which are different from the materials/material combinations used in surface section 22, for producing a second sensitivity, for example with respect to $NO+NO_2$. Typical layer thicknesses of the gate metal platings in surface sections 22, 24 are between 10 nm and 200 nm, preferably between 30 nm and 100 nm.

Alternatively, instead of using two different materials/material combinations, different sensitivities may be produced by using porosities and/or morphologies of metallic gate 16 in surface section 22 that is/are different from that/those of metallic gate 16 in surface section 24.

Connection to a working point AP having gate voltage $U_G$ of 2 volts, for example, at a drain-source voltage $U_{DS}$ of 15 volts, for example, produces a depletion zone in semiconductive channel 10 in the drain region (region of the first electrode), so that surface section 24 of the gate electrode is active having a sensitivity to $NO+NO_2$, and influences the channel conductive characteristics, depending on the detected. gas concentration.

A comparison with the similar illustration of FIG. 2 for pole reversal of drain-source voltage $U_{DS}$ shows that in this second operating state, once again on the characteristic curve of gate voltage $U_G$ of 2 volts, the depletion region (depletion zone) in channel semiconductor 10 has moved toward the source electrode, so that, compared to the first operating state of FIG. 1, it is no longer surface section 24 of the gate electrode, but, rather, surface section 22 of the gate electrode which is active. Since this surface section is sensitive to NO according to the setup of the semiconductor shown as an example, the generated sensor signal (current flow through the channel) is different from the wiring state (operating state) of FIG. 1, so that by comparing both signals, in particular forming a difference and thus averaging the NO component, the described system of the first exemplary embodiment allows reliable and compensated detection of $NO_2$.

Figure 4:
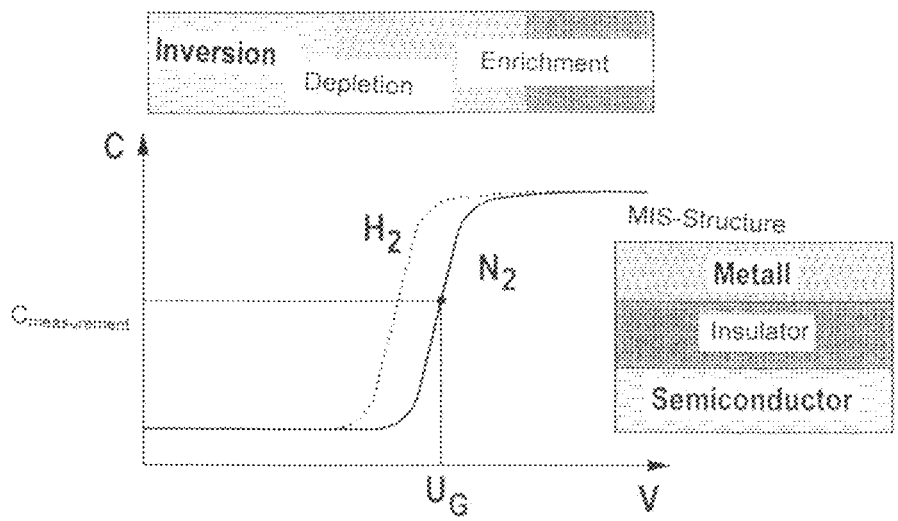
FIG. 4 shows a capacitance-voltage diagram for an MIS structure when acted on by two different gases, for clarifying the action in the region of depletion.
Figure 5:
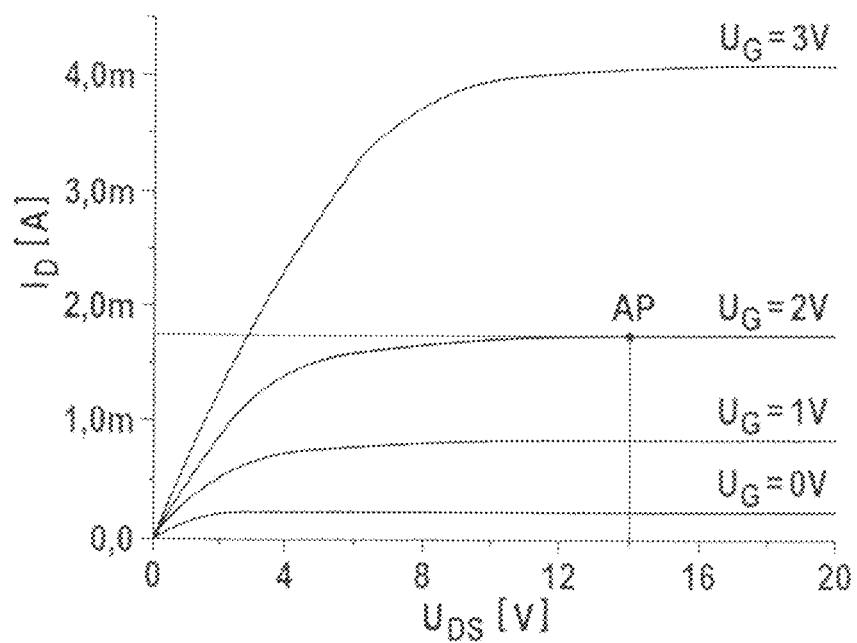
FIG. 5 shows a current-voltage characteristic map of a CHEMFET for clarifying a typical working point setting.

FIGS. 3 and 4 clarify the characteristic of a CHEMFET, which may advantageously be utilized within the scope of the present invention, that only (gate) surface sections situated in the depletion region of the channel effectively contribute to the channel conductivity, thus allowing the selective evaluability or switchability according to the present invention between the two surface sections (in this regard, the schematic diagram of FIG. 3 shows a generic FET with associated band diagrams on the source and drain sides, and FIG. 4 shows changes in capacitance, as a function of the channel geometry, as the result of simulations).

Figure 6:
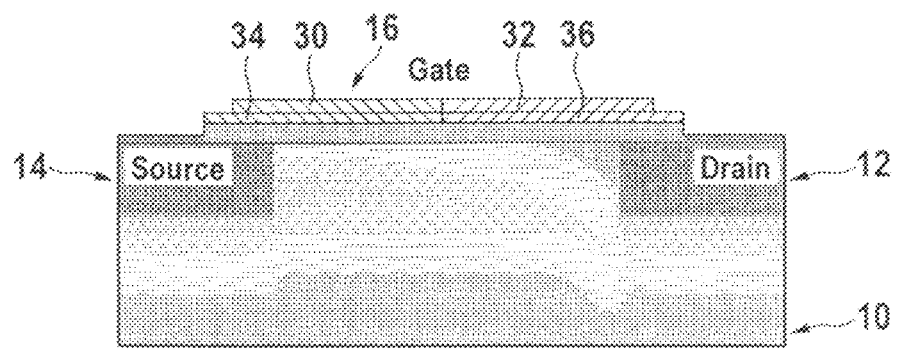
FIG. 6 shows a schematic illustration of a second exemplary embodiment of the present invention.

FIG. 6 shows a second exemplary embodiment of the present invention; corresponding elements have been provided with the same reference numerals as in FIGS. 1 and 2. In this particular exemplary embodiment in FIG. 6, once again a gate electrode is provided which is divided into two surface sections 30, 32, and the plating of the gate electrode is porous and designed in such a way that each gas to be detected is able to penetrate through the gate electrode to the surface of the underlying gate stack layer on the insulator layer. Here as well, however, the gate stack layer surface is geometrically divided into two sections 34, 36 corresponding to surface sections 30, 32, and is provided with materials of differing gas selectivity (sensitivity). Gate stack surface layer 34, 36 is produced from electrically insulating materials, for example, from oxides such as silicon dioxide ($SiO_2$), aluminum oxide ($Al_2O_3$), hafnium oxide ($HfO_2$), tantalum oxide ($Ta_2O_5$), or zirconium oxide ($ZrO_2$), and/or from nitrides such as silicon nitride ($Si_3N_4$) or boron nitride (BN), for example, and/or from carbides such as silicon carbide, for example, and/or from silicides such as tungsten silicide ($WSi_2$) or tantalum silicide ($TaSi_2$), for example. Different doping of the two gate stack surface layers 34 and 36 using metals such as Pt or Pd, for example, may also contribute to gate regions 30 and 32 having different sensitivities or selectivities. Typical layer thicknesses of the gate stack surface layers are in a range of 10 nm to 500 nm, preferably 20 nm to 100 nm.

The present invention is not limited to the examples shown with reference to the figures; rather, numerous variations of the present invention are possible by suitably forming surface sections of the gate electrode, the gate insulation layer, and/or the gate stack surface; the present invention is also not limited to the symmetrical configuration shown; rather, the division into the surface sections may be suitably varied on one of the two channel electrodes.

In particular, achieving different sensitivities for gases in the surface sections is also encompassed by the present invention by implementing a region (corresponding to one of the surface sections) in a gas-blind manner, for example, by using a closed metal film, so that, using a gate which is gas-sensitive on only one side, the present invention allows a semiconductor device to be implemented in which a gas sensitivity may be switched on and off.

If the gate region is plated using a closed metal film on one or both sides, as an alternative to a completely gas-blind design primarily the detection of hydrogen is a possibility, while (otherwise known) porous (in particular nanoporous), catalytically active gate platings are also suitable for numerous hydrogen-containing gases (for example, ammonia, hydrocarbons, and others) as well as for oxygen-containing gases (such as nitrogen oxides, carbon monoxide, etc.). An implementation is also possible in which a first sensitivity of a first surface section with respect to nitric oxide is combined with a second sensitivity (corresponding to a second of the surface sections) with respect to hydrogen selectivity, so that, for example, a semiconductor component may be produced which is switchable between suitability as an NO detector and suitability as an $H_2$ detector.

What is claimed is:

1. A gas-sensitive semiconductor device, comprising:
   a semiconductive channel which is delimited by a first and a second channel electrode; and
   a gate electrode which is associated with the channel and which cooperates with the channel in such a way that a change in conductivity of the channel occurs as a response to an action of a gas;
   wherein at least one of the gate electrode and a gate insulation layer which insulates the gate electrode from the channel has two surface sections which differ in their sensitivity to gases,
   wherein at least one of the gate electrode, the gate insulation layer and a gate stack layer which is provided between the gate electrode and the channel has two surface sections which differ in their sensitivity to gases, and
   wherein the gate electrode is divided into two regions which are made of different materials and which correspond to the two surface sections, a region junction of the regions being situated between the channel electrodes.

2. The device as recited in claim 1, wherein the semiconductor device is a semiconductor component in the form of a field effect transistor (FET), the channel electrodes implementing the drain and the source of the FET.

3. The device as recited in claim 2, wherein the FET is a CHEMFET.

4. The device as recited in claim 1, wherein the region junction is situated transverse to a direction of extension of the channel.

5. The device as recited in claim 2, wherein the gate electrode is divided into two regions which are made of different materials and which correspond to the two surface sections, a region junction of the regions being situated between the channel electrodes.

6. A gas-sensitive semiconductor device, comprising:
   a semiconductive channel which is delimited by a first and a second channel electrode; and
   a gate electrode which is associated with the channel and which cooperates with the channel so that a change in conductivity of the channel occurs as a response to an action of a gas;
   wherein at least one of the gate electrode and a gate insulation layer which insulates the gate electrode from the channel has two surface sections which differ in their sensitivity to gases,
   wherein at least one of the gate electrode, the gate insulation layer and a gate stack layer which is provided between the gate electrode and the channel has two surface sections which differ in their sensitivity to gases, and wherein for implementing the two surface sections the gate electrode contains different metals or metal platings.

7. The device as recited in claim 2, wherein for implementing, the two surface sections the gate electrode contains different metals or metal platings.

8. The device as recited in claim 1, wherein for implementing the two surface sections, the gate electrode contains different metals or metal platings.

9. A gas-sensitive semiconductor device, comprising:
a semiconductive channel which is delimited by a first and a second channel electrode; and
a gate electrode which is associated with the channel and which cooperates with the channel so that a change in conductivity of the channel occurs as a response to an action of a gas;
wherein at least one of the gate electrode and a gate insulation layer which insulates the gate electrode from the channel has two surface sections which differ in their sensitivity to gases,
wherein at least one of the gate electrode, the gate insulation layer and a gate stack layer which is provided between the gate electrode and the channel has two surface sections which differ in their sensitivity to gases, and
wherein one of the two surface sections of the gate electrode has a gas-tight metal plating.

10. The device as recited in claim 2, wherein one of the two surface sections of the gate electrode has a gas-tight metal plating.

11. The device as recited in claim 1, wherein one of the two surface sections of the gate electrode has a gas-tight metal plating.

12. A gas-sensitive semiconductor device, comprising:
a semiconductive channel which is delimited by a first and a second channel electrode; and
a gate electrode which is associated with the channel and which cooperates with the channel so that a change in conductivity of the channel occurs as a response to an action of a gas;
wherein at least one of the gate electrode and a gate insulation layer which insulates the gate electrode from the channel has two surface sections which differ in their sensitivity to gases,
wherein at least one of the gate electrode, the gate insulation layer and a gate stack layer which is provided between the gate electrode and the channel has two surface sections which differ in their sensitivity to gases, and
wherein at least one of the surface sections of the gate electrode has a nanoporous or catalytically active plating.

13. A gas-sensitive semiconductor device, comprising:
a semiconductive channel which is delimited by a first and a second channel electrode; and
a gate electrode which is associated with the channel and which cooperates with the channel so that a change in conductivity of the channel occurs as a response to an action of a gas;
wherein at least one of the gate electrode and a gate insulation layer which insulates the gate electrode from the channel has two surface sections which differ in their sensitivity to gases,
wherein at least one of the gate electrode, the gate insulation layer and a gate stack layer which is provided between the gate electrode and the channel has two surface sections which differ in their sensitivity to gases, and
wherein the gate electrode has a porous metal plating, and for implementing the two surface sections the gate stack electrode contains different surface materials.

14. A gas-sensitive semiconductor device, comprising:
a semiconductive channel which is delimited by a first and a second channel electrode;
a gate electrode which is associated with the channel and which cooperates with the channel so that a change in conductivity of the channel occurs as a response to an action of a gas; and
an adjusting arrangement to adjust the working point by applying a first electrical voltage having a first polarity in a first operating mode between the first and the second channel electrode, the arrangement being configured for adjusting the working point for the controlled application of a second electrical voltage having a second polarity opposite the first polarity in a second operating mode;
wherein at least one of the gate electrode and a gate insulation layer which insulates the gate electrode from the channel has two surface sections which differ in their sensitivity to gases, and
wherein at least one of the gate electrode, the gate insulation layer and a gate stack layer which is provided between the gate electrode and the channel has two surface sections which differ in their sensitivity to gases.

15. The device as recited in claim 2, further comprising:
an adjusting arrangement to adjust the working point by applying a first electrical voltage having a first polarity in a first operating mode between the first and the second channel electrode, the arrangement being configured for adjusting the working point for the controlled application of a second electrical voltage having a second polarity opposite the first polarity in a second operating mode.

16. The device as recited in claim 1, further comprising:
an adjusting arrangement to adjust the working point by applying a first electrical voltage having a first polarity in a first operating mode between the first and the second channel electrode, the arrangement being configured for adjusting the working point for the controlled application of a second electrical voltage having a second polarity opposite the first polarity in a second operating mode.

17. The device as recited in claim 14, further comprising:
an electronic evaluation arrangement for detecting operating signals of the semiconductor device in the first and the second operating modes, and for comparing these operating signals or forming a difference between these operating signals.

18. The device as recited in claim 17, wherein the operating signals are channel currents flowing during operation.

* * * * *